United States Patent [19]
Denance

[11] Patent Number: 5,300,029
[45] Date of Patent: Apr. 5, 1994

[54] ELECTROMECHANICAL INJECTION APPARATUS FOR MEDICAL AND VETERINARY USE ACTUATED BY A TRIGGER

[76] Inventor: Raymond Denance, Le Commodore H41, Marina Baie des Anges, 06270 Villeneuve Loubet, France

[21] Appl. No.: 83,293

[22] Filed: Jun. 29, 1993

[30] Foreign Application Priority Data

Jul. 1, 1992 [FR] France .................................. 92 08339

[51] Int. Cl.$^5$ .............................................. A61M 5/00
[52] U.S. Cl. .................................... 604/117; 222/333; 128/DIG. 1; 604/155
[58] Field of Search ............... 604/117, 155, 187, 198, 604/211, 210, 207, 208; 222/333, 390; 128/DIG. 1

[56] References Cited

U.S. PATENT DOCUMENTS

4,931,041  6/1990  Faeser ........................ 128/DIG. 1
5,034,003  7/1991  Denance ............................ 604/117

Primary Examiner—Jerome L. Kruter
Attorney, Agent, or Firm—Young & Thompson

[57] ABSTRACT

An electromechanical injection device for medical and veterinary use comprises a frame (1) having the shape of a pistol provided with a stock (2) and bearing a movable carriage (3) that supports a removable syringe (4) having a needle (5) and a piston (6). A first motor (7) actuates a pusher (8) which acts against the piston (6) of the syringe (4). A cradle (9) is carried by the frame (1) and supports the syringe (4) on the movable carriage (3). A second motor (12) actuates the movable carriage (3). The forward portion of the frame has a stabilizing sight (10) for application to the skin which guides and predetermines the degree of penetration of the needle (5). An adjustment wheel (11) permits adjusting the position of the sight (10) to adjust the depth of penetration of the needle (5). A trigger (18) actuates the motors (7, 12). The second motor (12) is fixed to the frame (1) and has a rotatable axle (30) and a first cam (29) on that axle. The second motor (12) drives, via that axle (30) and the first cam (29), the movable carriage (3) in movement lengthwise of the frame (1). There is a second cam (26) on the trigger (18). The first and second cams (29, 26) coact with each other according to the translated position of the trigger (18) to control advancement of the piston (6).

6 Claims, 6 Drawing Sheets

ELECTROMECHANICAL INJECTION APPARATUS FOR MEDICAL AND VETERINARY USE ACTUATED BY A TRIGGER

BACKGROUND OF THE INVENTION

The invention has for its object an electromechanical injection device for medical and veterinary use actuated by a trigger.

DESCRIPTION OF RELATED ART

The state of the art can be defined by the following patents:

FR-A-2.524.321: The invention describes an injection device usable either for manual injection or for mechanical injection characterized in that it comprises: a stock construction having the shape of a pistol, a removable injection syringe provided with a syringe piston, a single injection needle or a multi-injector having several injection needles, a syringe cradle rendering this syringe fixed to the stock construction, means to position the impact and to predetermine the degree of penetration of the needle or the needles, mechanical transmission means comprising a catch and a small barrel transmitting the pressure exerted to trigger the penetration of the needle or needles and the injection of the liquid.

FR-A-2.567.760: The invention describes an apparatus of the type comprising a construction having the general shape of a pistol provided with a stock and receiving a movable carriage for a removable syringe with a needle and piston. It is characterized in that it is provided with a single drive element, here a fluid distributor, connected solely to a pusher maintained in bearing against the piston of the syringe. The kinematic linkage is of the one-way type. The carriage is associated with an abutment fixed at a distance less than the total possible path of the piston. Thus, in the reciprocating direction, the pusher when driven pushes the piston-syringe-carriage assembly while bearing on the product placed in the syringe. When the carriage encounters the abutment, it stops and immobilizes the syringe, but the pusher continues its path and now requires the product to flow through the needle. In the front-to-rear position, a rod integral with the piston returns the carriage by an abutment that it carries and this drives the syringe-piston-pusher assembly (this latter again being free) to return rearwardly at the same time. The carriage and the syringe resume their start position while the piston returns a bit farther, by a distance which is a function of the dose of product injected by it during the preceding rear-to-front movement.

FR-A-2.390.175: The invention describes an injection device for automatic injection. This device operates step by step or by a series of shots, it is preferably disposed in a frame and comprises an injection syringe preferably removable and interchangeable, and first motor means and second motor means actuating this latter in alternate directions of displacement.

FR-A-2.594.341: The invention describes an apparatus comprising an injection head bearing a needle connected to a syringe with a piston. A pneumatic microjack with a rod controls the movement of the needle for injection. A reversible micromotor controls the speed and amplitude of displacement of the piston to adjust the quantity and the flow rate of the fluid medication which the syringe delivers from the needle. The operation of the micromotor and of the microjack is under the control of an electronic control center. It is possible to program continuous injections, with timed retraction and by doses of variable cadence.

FR-A-2.622.457: The invention describes a device controlled by a microprocessor to administer or remove liquid products as well as micro-currents. It is constituted by a frame whose upper removable portion encloses a syringe provided with a needle. An electronic micro-circuit controls the operation of an electric motor which actuates a rack ensuring the penetration and the retraction of the needle, and an electric motor which actuates a rack actuating the piston. Potentiometers actuate the piston. Potentiometers program respectively the power and the length of operation of the motor, the synchronization of the motors, the threshold of sensibility of an electronic circuit sensitive to variations of conduction at the point of the needle as well as the intensity of a current engendered by a second electronic circuit.

FR-A-2.348,709: The invention relates to an injection device forming an automatic micro-injector. This device operates step by step or by a series of shots. It is disposed preferably in a frame of the shape of a pistol and comprises an injection syringe preferably removable and interchangeable, and motor means actuating this latter in reciprocating displacement.

FR-A-2.639.234: The invention relates to an injection device of the electric type comprising a stock frame, a syringe which rests on the upper horizontal surface of the stock frame and is maintained as to its forward portion by its ferrule which rests on a cradle and in the rear part by the head of the piston of the syringe which is disposed in a movable slide actuated by an electric motor which transmits the pressure to start the penetration of the needle and the injection of the liquid, a sight for stabilizing the skin guides and predetermines the degree of penetration of the needle by an adjustment characterized by the fact that the stabilizing sight is of the removable type, a maintaining means actuating as a spring ensuring its maintenance in a hollow micrometric screw, itself disposed in a movable cylinder, said movable cylinder comprising a movable finger which acts on means serving as a value disposed at the level of the injection needle. The head of the piston of the syringe is in contact with the head of a piston located in the movable slide, the piston is provided with a spring mounted coaxially of the piston rod, said spring is disposed in the movable slide, the slide assembly and piston is actuated by the electric motor which acts on a threaded axle, on which is mounted the body of the slide which forms at this point a maneuvering nut.

These different devices or guns are applicable particularly to mesotherapy.

They permit continuous, timed or repetitive injections, or injections step by step.

The patent FR-A-2.633.234 describes a gun which operates without a trigger, the penetration of the needle and the beginning of injection are effected by simple pressure of the assembly of the gun and by retraction of the sight.

U.S. Pat. No. 4,613,328 describes a biomedical injection apparatus. This apparatus uses a motor which actuates the piston of the syringe. An electronic circuit associated with an electronic brain permits managing the operations of the biomedical injection apparatus.

The principal drawback resides in the fact that it is necessary to raise the gun each time, which is to say to interrupt the contact between the sight and the skin, to reactivate the device. This can pose problems in the case in which delicate and very precise surfaces are treated, for example on the face as well as by step-by-step injection, or continuous injection or timed or repetitive injection.

As to other guns that have a trigger, they use electric magnets and/or a pneumatic mechanism. These embodiments are too heavy (electromagnet, windings, $CO_2$ supply, etc.) whether or not they are manual, they are connected by tubes to compressors, and hence hardly practical.

The invention seeks to solve these drawbacks.

The device according to the invention permits three modes of operation actuated by the trigger, therefore without the need to remove the sight from contact with the skin:

continuous injection, step-by-step injection with predetermined dosages, timed or repetitive injection, the timing of the cycle being adjustable.

Moreover, the device according to the invention permits reducing by half the weight of the apparatus relative to equivalent guns. Thus, the device according to the invention uses electromechanical means such as electric motors and cam sets.

SUMMARY OF THE INVENTION

The electromechanical injection device for medical and veterinary use is of the type comprising a frame having the general shape of a pistol provided with a stock and receiving a movable carriage for a removable syringe with a needle and piston, at least one motor element actuating a pusher which acts against the piston of the syringe and a cradle providing sliding support for the syringe mounted on the movable carriage, actuated itself by another motor element, the forward portion of the pistol being provided with a stabilizing sight for the skin which guides and predetermines the degree of penetration of the needle by an adjustment nut which permits adjusting the depth of entry of the securement end of the sight, an electric motor actuates the piston of the syringe and is fixed to the movable carriage, its axle actuates a gear train mounted on said movable carriage, characterized by the fact that the other electric motor fixed to the frame acts, by its axle, on a cam set which drives the movements of the movable carriage. The movements of the movable carriage are modified by actuating the trigger of the pistol. The trigger has its axis parallel to the axle of the motor which drives the movements of the movable carriage. The piston determines the type of injection (continuous injection, step-by-step injection with predetermined doses, timed injection or repetitive injection with adjustable timing).

The trigger of the pistol is mounted for rotation and axial displacement, it is provided with a cam whose displacement in rotation acts on another cam mounted on the drive motor axle for the movable carriage which is actuated in rotation and in translation and which, as a function of the angular position of the trigger cam, acts to advance the carriage one step or reciprocatingly by escapements.

The cam mounted on the motor axle is a cam for transforming movement of rotation to translatory movement; to this end, it has a shape of a ring to be received about the motor axle and comprises at least one helicoidal groove which coacts with a lug secured to said motor axle, it is provided with two lateral ears, said cam also serves as an abutment to come into abutment against a movement tongue of the movable carriage.

The movable carriage is mounted slidingly on the frame of the pistol, a return spring is interposed between said body of the movable carriage and a wall of the frame, so as to return said movable carriage to the rear.

The trigger is comprised by a free portion as a external wheel manipulable in rotation and in translation and a second free portion manipulable only in translation.

Said portion free for rotation and translation, which is located parallel to the interior of the body of the pistol, comprises a lug disposed perpendicularly to the axis of the trigger and which serves, according to an angular position, to limit the translatory displacement of said axle of the trigger.

A second portion of the axle, which is free only in translation, also comprises a lug which coacts with a cam in the shape of a ring provided with at least one helicoidal groove in which said lug is disposed.

The ring-shaped cam comprises a positioning finger which, as a function of the more or less great insetting of the axle of the trigger, is displaced in a solely angular manner because it is blocked in translation so as either to displace the cam mounted on the motor axle, so that it will come into abutment against the manipulating tongue of the movable carriage and advance it for continuous or step-by-step injection, or come to act against the two lateral ears to advance this cam ring so that it comes into abutment against the manipulating tongue and causes the movable carriage to advance, until the positioning finger escapes the lateral ears which are in rotation with the cam ring driven by the axle of the motor, to commence a new cycle as soon as the positioning finger again encounters the lateral ears so as to obtain reciprocatory movement of the carriage corresponding to the timed or repetitive injection.

DESCRIPTION OF THE PREFERRED EMBODIMENT

The electromechanical injection device for medical and veterinary use, such as shown in FIGS. 1 to 7, is of the type comprising a frame 1 having the general shape of a pistol provided with a stock 2. The stock comprising the electronic portion is not shown. This frame 1 receives a movable carriage 3 for a removable syringe 4 with a needle 5 and piston 6, at least one motor element such as an electric motor 7 actuates a pusher 8 which acts against the piston 6 of the syringe. The syringe 4 is mounted on a cradle 9 which serves to support said syringe 4. Said cradle is fixed to the movable carriage 3. The pusher 8 is mounted slidingly on a screw-threaded rod 16 which is itself actuated by said motor 7.

The forward pusher of the pistol is provided with a stabilizing sight 10 for the skin which guides and predetermines the degree of penetration of the needle 5 by an adjustment wheel 11 which permits adjusting the depth of entry of the securement end of the sight 10. All these different means are known in the art.

In the embodiment shown in the drawings, the motor 7 is secured to the movable carriage 3. It moves with this latter.

The motor 7 is supplied by a battery or by an electrical connection which can be effected through the outlet 13 of the stock 2 of the pistol.

The axle of the motor 7 actuates a gear train 14, 15 also mounted on the frame 3. The gear 15 turns the threaded rod 16, which displaces the follower 17, which is secured to the pusher 8 which actuates the piston 6 of the syringe 4.

The other motor 12 is fixed to the frame 1 in contrast to motor 7 which is fixed to the movable carriage 3.

This motor 12 acts, by its axle 30, on the cam 29 with ears 32, 33 which drive the movements of the movable carriage 3. The movements of the movable carriage 3 are modified by actuating the trigger 18 of the pistol.

Figure 2:
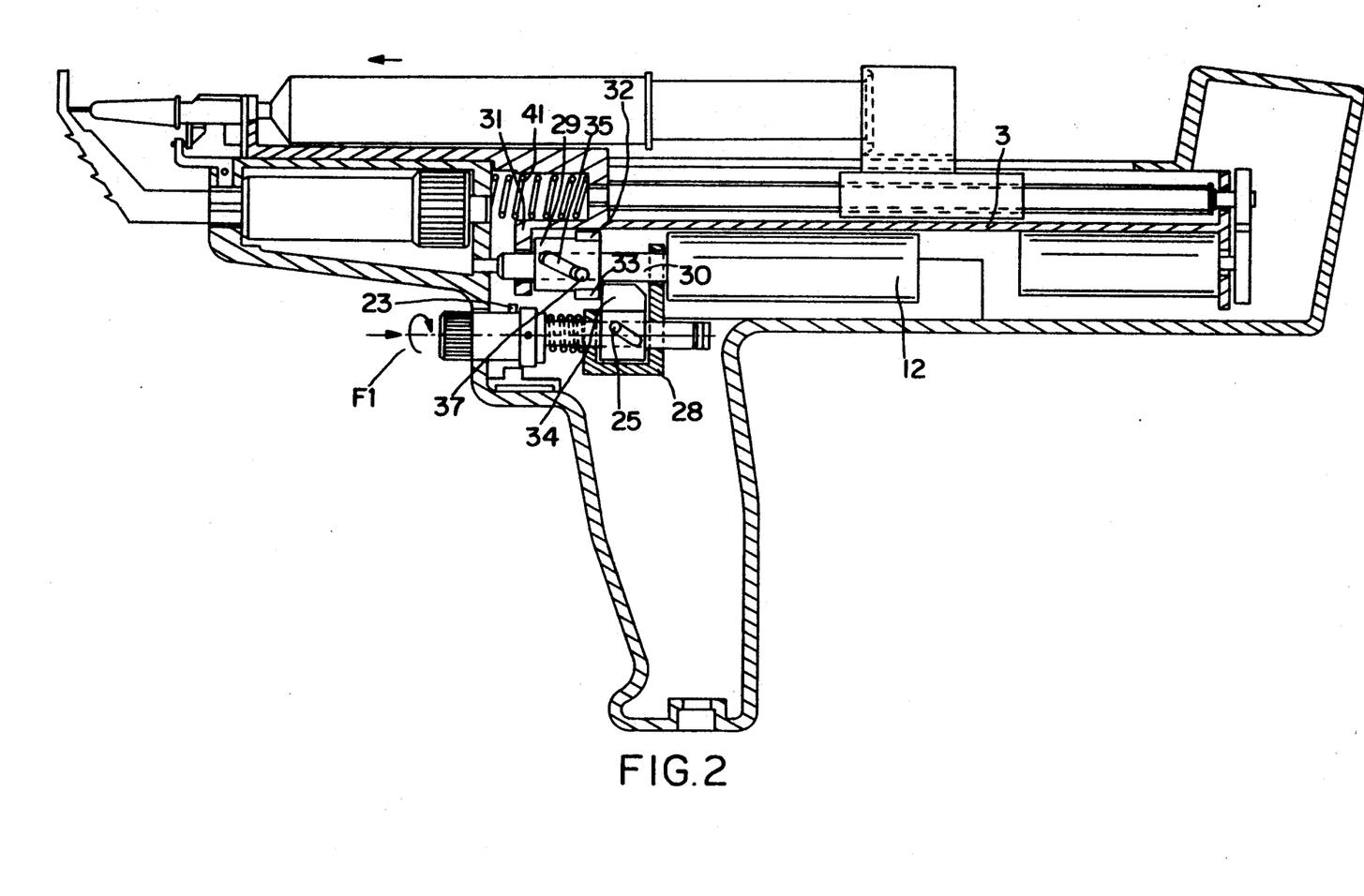
FIG. 2 is a schematic view of the device when the user pulls the trigger and when this latter is pushed in, the positioning finger is completely raised, it displaces in translation the cam with the ears mounted on the motor axle which then presses the manipulating tongue of the carriage forward. The positioning finger blocks, in return, the assembly of the cam over all the circular periphery of the cam ring. This view corresponds to step-by-step or continuous injection.
Figure 3:
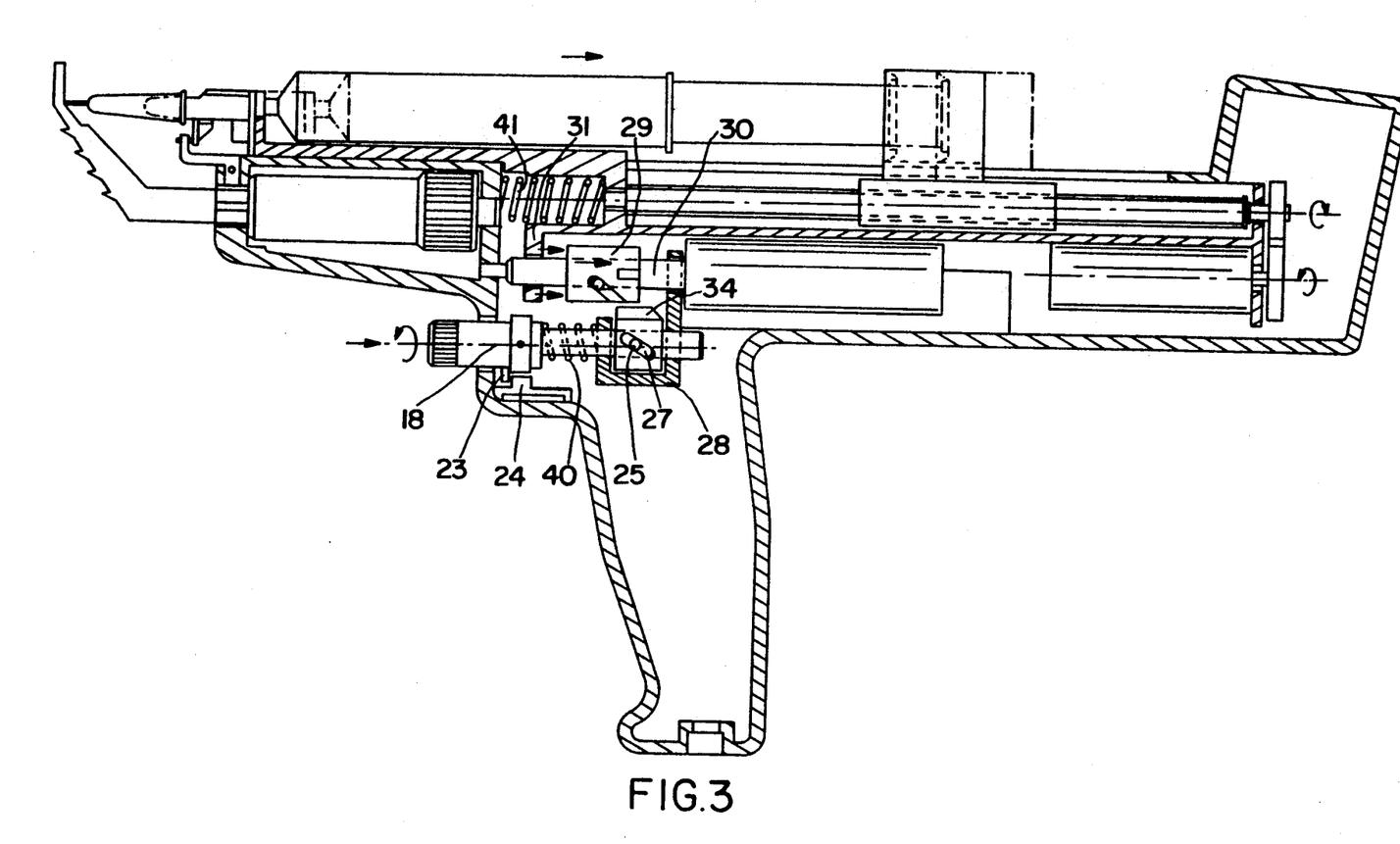
FIG. 3 is a view of the device in which the trigger is pushed half-way in, because it comes into abutment after having been rotated. In this position, the positioning finger is in contact only with the lateral ears of the cam and it escapes very rapidly from these lateral ears, and by its return spring, the carriage returns rearwardly. This view corresponds to timed or repetitive injection.
Figure 4:
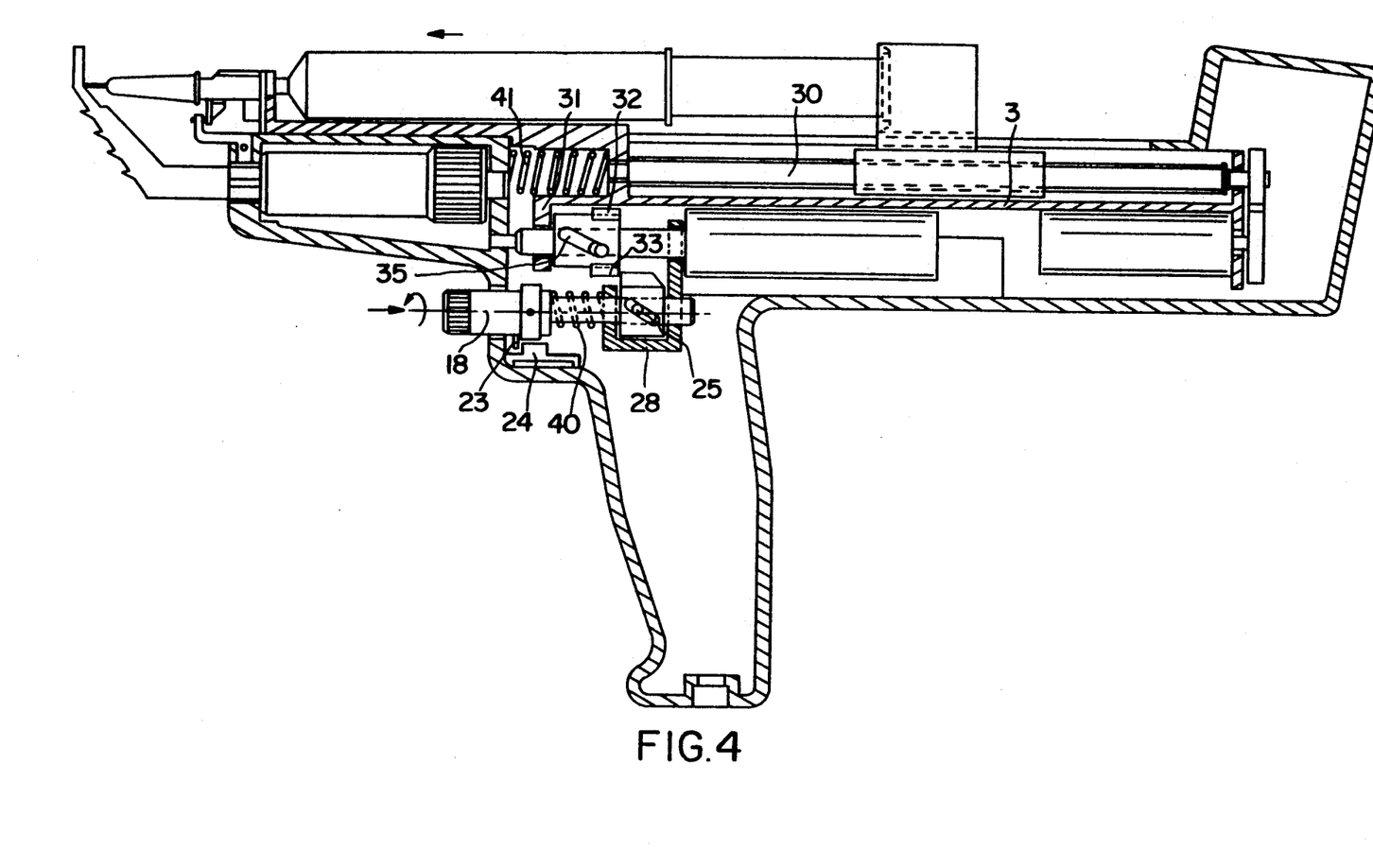
FIG. 4 is a view according to FIG. 3 showing the action of the positioning finger and the lateral ears, which displace the cam in translation, to push the manipulating tongue and cause the carriage to advance forwardly.
Figure 5:
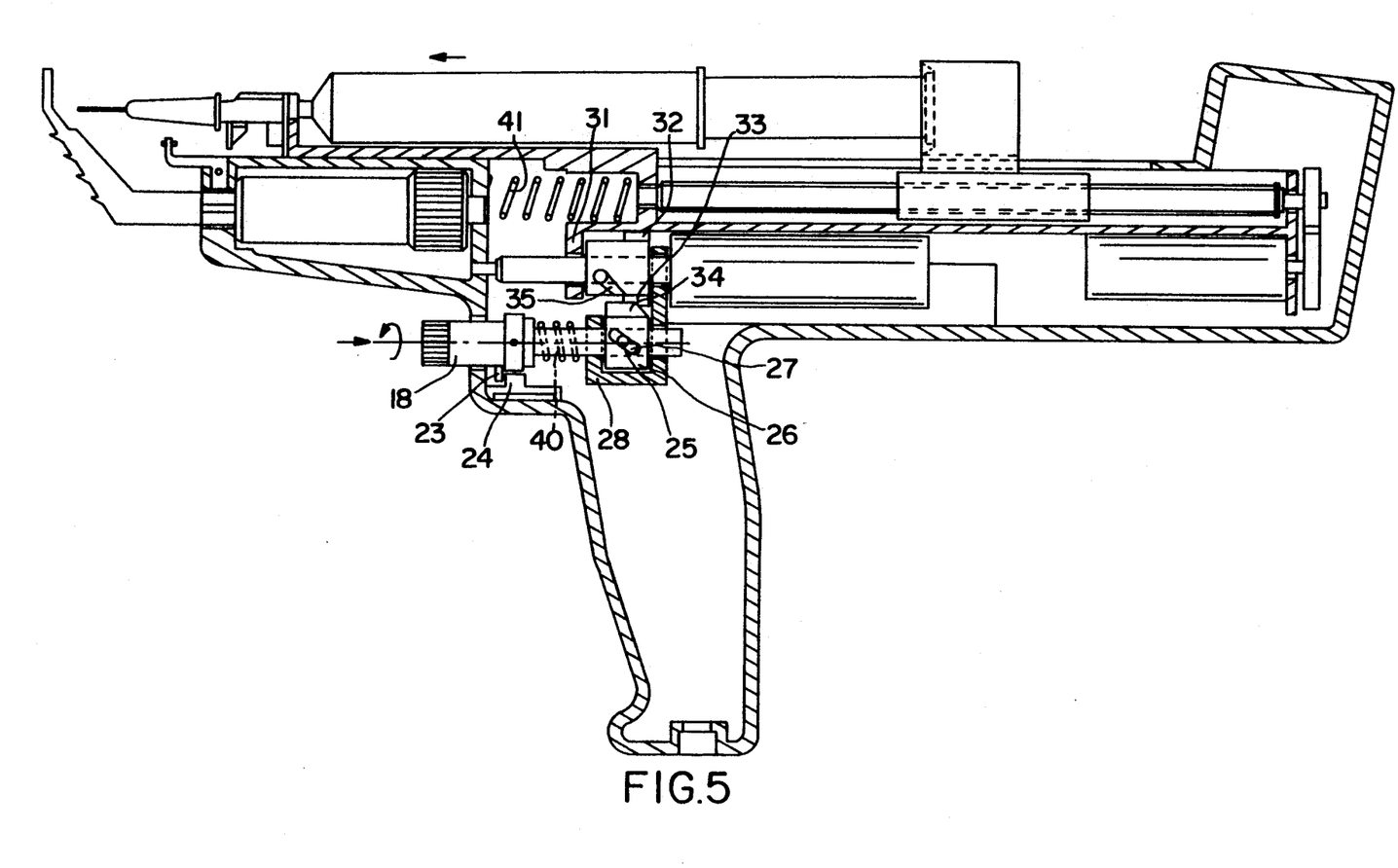
FIG. 5 is a view similar to FIGS. 3 and 4 in which the carriage is returned to the rear, after which the positioning finger will have escaped from the lateral ears of the cam. Said lateral ears will come into abutment again against the positioning finger and block in rotation and will again displace the cam in translation so that the latter will again advance the movable carriage by abutting against the manipulating finger of said carriage disposed in the path of translation of the cam slidably mounted on the motor axle.
Figure 6:
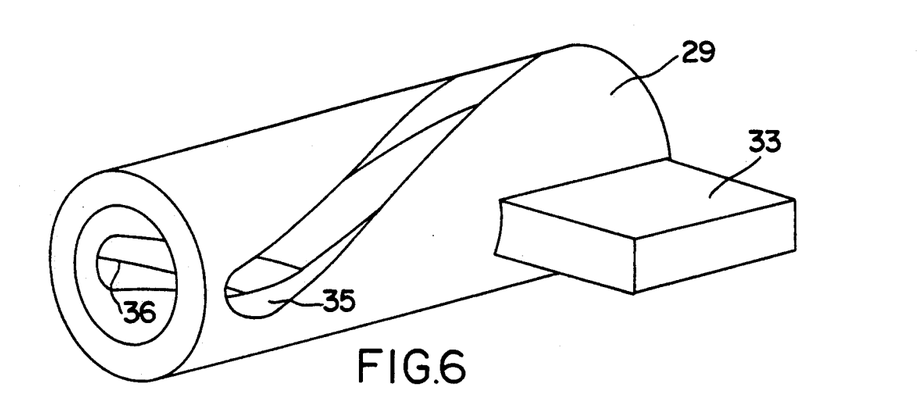
FIG. 6 is a perspective view of the ring-shaped cam mounted on the motor axle, which is a cam for transformation of rotating movement into angular movement; it comprises two helicoidal lateral grooves and two lateral ears.
Figure 7:
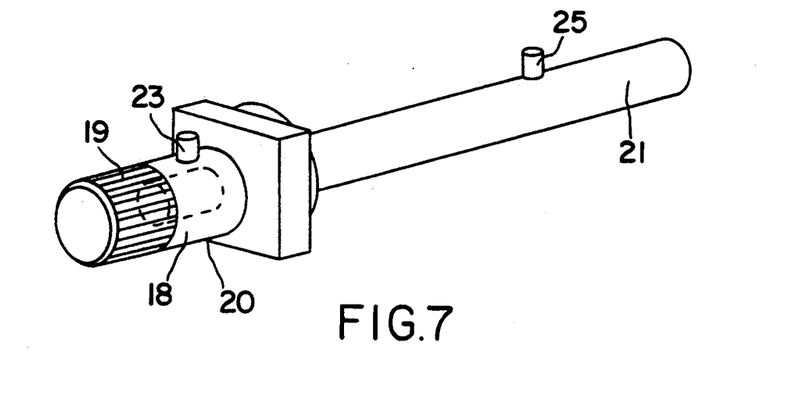
FIG. 7 is a view of the trigger with its two parts, the first which is free in rotation and in translation, and the second which is free only in translation.
Figure 8:
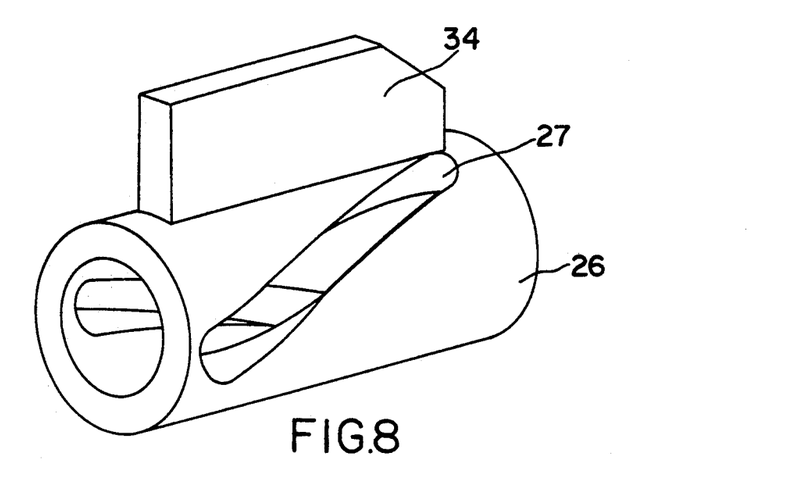
FIG. 8 is a perspective view of the ring-shaped cam mounted on the second part of the axle of the trigger; it is provided with a positioning finger. Said cam is actuated in rotation by two lugs secured to the axle and two helicoidal lateral grooves, this cam is not free in translation.

The trigger 18 is comprised of a free portion such as an external wheel 19 manipulable in rotation, as indicated by the arrow F1 (FIG. 2). This first portion 20 is therefore free in rotation and in translation. The second portion 21 of the trigger 18 is free only in translation. The portion 20 free in rotation and in translation is located partially in the internal space 22 of the stock of the pistol. It comprises a lug 23 disposed perpendicularly to the axis of the trigger 18. Said lug 23, according to its angular position, will limit the displacement in translation of the assembly of the trigger 18 and this because the lug 23 can strike against the abutment 24, as shown in FIGS. 3 and 4. With this angular position, the trigger 18 can be only partially pushed in.

The second portion 21 of the axle of the trigger, which is free only in translation, comprises two diametrically opposed lugs 25, perpendicular to the longitudinal axis of the trigger 18. These two lugs 25 coact with a ring-shaped cam 26 provided with two lateral helicoidal grooves 27 in which said lugs 25 are disposed. The cam 26, in the shape of a ring, comprises at its periphery a longitudinal positioning finger 34 which, as a function of the translated position of the axle of the trigger 18, will move only in an angular manner because said ring-shaped cam 26 is blocked in translation in a recess 28 (FIG. 2). This ring-shaped cam 26, with its positioning finger 34, will, according to the angular orientation of the positioning finger:

either displace the cam 29 (FIG. 2) which is mounted on the axle 30 of the motor 12, so that the latter will come into abutment against the manipulating tongue 31 of the movable carriage 3 and cause it to advance for continuous injection or for step-by-step injection, or will act against the two lateral ears 32 and 33 to cause the cam 29 to advance, so that it will come into abutment with the manipulating tongue 31 and cause the movable carriage 3 to advance, until the positioning finger 34 escapes from the two lateral ears 32 and 33 which are in rotation with the cam 29 driven by the axle 30 of the motor 12 so as to commence a new cycle as soon as the positioning finger 34 again encounters the lateral ears 32, 33 so as to obtain a reciprocating movement of the carriage 3 corresponding to timed or repetitive injection.

Ring-shaped cam 29 is a cam for the transformation of rotating movement into translatory movement. For this purpose, it has the shape of a ring encircling the axle 30, which is the axle of the motor 12. It comprises for this purpose two helicoidal grooves 35 and 36 each of which receives one of diametrically opposed lugs 37 perpendicular to the axle 30. These lugs 37 are fixed to the axle 30. According to the angular position of the positioning finger 34, this latter, by its more or less great height, will come either into abutment against the circular end of the cam 29 to make it displace in translation, and this latter thus encounters the manipulating finger 31 of the movable carriage 3, or, when the positioning finger 34 is less raised by its angular position, simply into abutment against the lateral ears 32 and 33, giving rise, as explained above, to reciprocating movement of the movable carriage 3.

The manner of operation of the device according to the invention is as follows:

Continuous injection:

The user pushes on the trigger 18. Immediately, the motors 7 and 12 are actuated. The motor 7 controls the injection of the product by translation of the piston of the syringe. The motor 12 controls the penetration of needle 5 by translation of the movable carriage 3 bearing said syringe 4.

Figure 1:
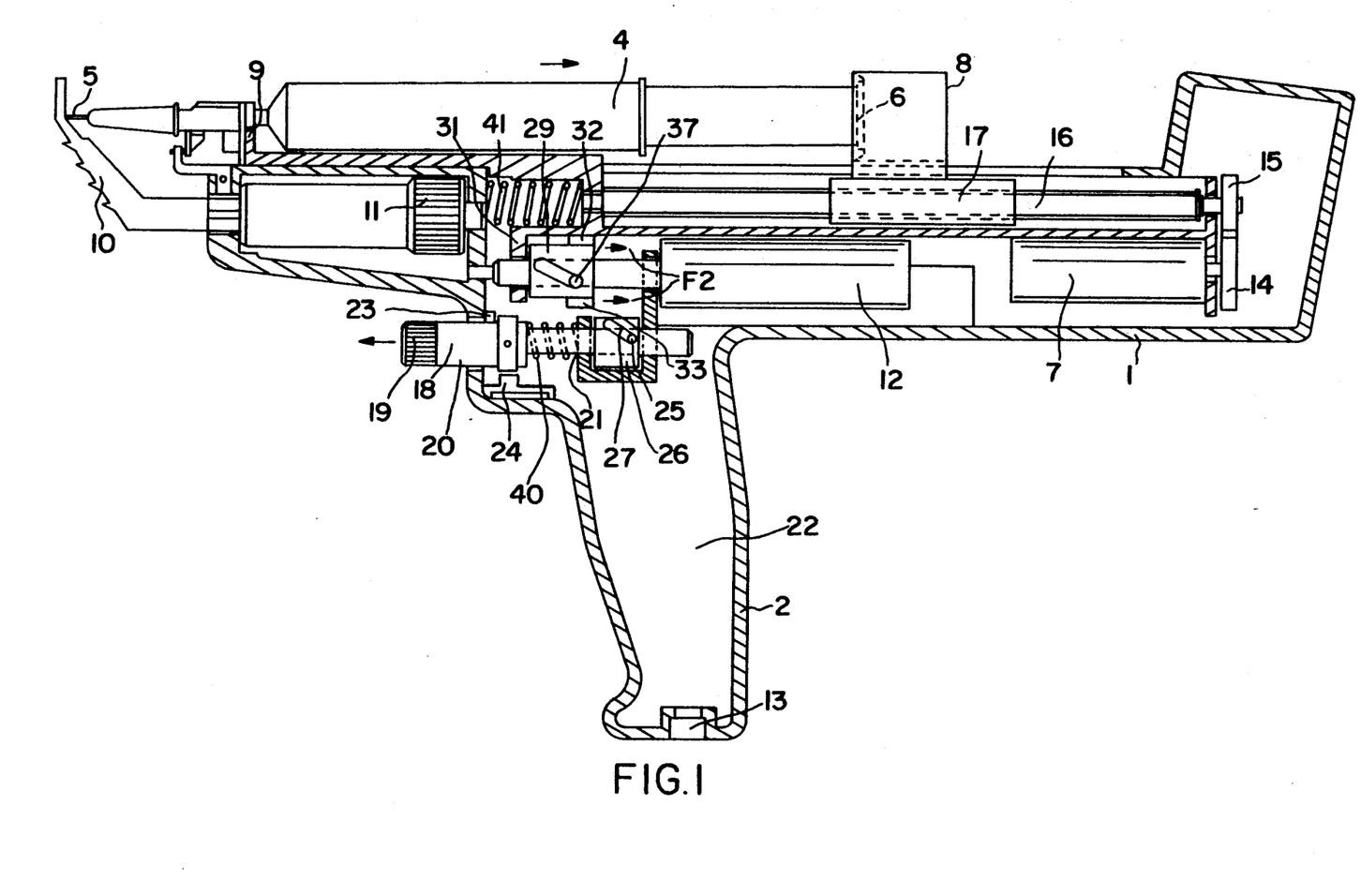
FIG. 1 is a theoretical schematic view of the stopping device when the trigger is released and when the syringe-carrying carriage will immediately return to the rear (see the arrows F2).

While the trigger 18 is maintained depressed, the movable carriage 3 remains in the advance position and the piston 6 of the syringe 4 advances. Upon releasing trigger 18, as shown in FIG. 1, the latter returns to its initial position thanks to the return spring 40. The cam 29, disengaged from the positioning finger 34, returns rearwardly, as indicated by the arrows F2 shown in FIG. 1. The manipulating tongue 31 is freed, the carriage 3 is returned rearwardly by its return spring 41, disposed between a portion of frame 1 and a shoulder of the carriage 3.

Step-by-step injection:

According to this mode of operation, one or several doses are preestablished with predetermined values. The dose is programmed by a button (not shown). The selected dose is indicated by luminous lamps.

The principle is the same as for continuous injection but, by contrast, when the dose is administered, while releasing the pressure on the trigger 18, the two motors 7 and 12 are stopped. The syringe 4 and the carriage 3 return at the same time as the product is no longer injected.

When the carriage 3 is returned, a new push on the trigger 18 permits recommencing a new step-by-step injection.

Timed or repetitive injection:

The user pushes on the trigger 18, the two motors 7 and 12 are actuated at the same time. The electromechanical reciprocating device, as described above, is applied to the movable carriage 3 which carries the syringe. The timing of this reciprocation is adjustable by a button (not shown).

What is claimed is:

1. In an electromechanical injection device for medical and veterinary use comprising a frame (1) having the shape of a pistol provided with a stock and along a longitudinal axis of said frame (2) and bearing a movable carriage (3) that supports a removable syringe (4) having a needle (5) and a piston (6), a first motor (7) actuating a pusher (8) which acts against the piston (6) of the syringe (4), a cradle (9) carried by the frame (1) and supporting the syringe (4) on the movable carriage (3), a second motor (12) actuating the movable carriage (3), the forward portion of the frame having a stabilizing sight (10) for application to the skin which guides and predetermines the degree of penetration of the needle (5), an adjustment wheel (11) which permits adjusting the position of the sight (10) to adjust the depth of penetration of the needle (5), and a trigger (18) to actuate said motors (7, 12); the improvement wherein said second motor (12) is fixed to the frame (1) and has a rotatable axle (30), a first cam (29) on said axle, said second motor (12) driving, via said axle (30) and said first cam (29) said movable carriage (3) in movement along said longitudinal axis of said frame (1), a second cam (26) on said trigger (18), said first and second cams (29, 26) coacting with each other according to the translated position of the trigger (18) to control advancement of said piston (6).

2. Device according to claim 1, wherein the trigger (18) is both rotatable and axially displaceable, and means (23, 24) in one rotated position of the trigger to prevent axial movement of the trigger.

3. Device as claimed in claim 1, wherein said first cam (29) is adapted to transform rotational movement into translatory movement and is in the form of a ring surrounding the axle (30) of the second motor (12) and has at least one helicoidal groove (35, 36) in which rids a lug (37) fixed to the axle (30) and has two lateral ears (32, 33) and is adapted to come into abutment against a manipulating tongue (31) of the movable carriage (3) to advance the carriage (3), said ears (32, 33) coacting with a positioning finger (34) on said second cam (26) to control the positioning of the carriage (3).

4. Device as claimed in claim 1, and a return spring (41) for urging said carriage rearwardly.

5. Device according to claim 1, wherein said trigger (18) is axially movable within said frame (1) and has a lug (25) which coacts with said second cam (26), said second cam (26) comprising a ring having at least one helicoidal groove (35, 36) in which said lug (25) is disposed.

6. Device according to claim 5, wherein said second cam (26) has a positioning finger (34) thereon which is adapted in one position to displace the first cam (29) so as to cause the first cam to advance the carriage (3) and in another position to act against lateral ears (32, 33) on the first cam to rotate the first cam to return the device to a position for a new cycle of operation.

* * * * *